United States Patent
Bond et al.

(10) Patent No.: US 8,526,709 B2
(45) Date of Patent: Sep. 3, 2013

(54) METHODS AND APPARATUS FOR DETECTING MULTIPLE OBJECTS

(75) Inventors: Robert Bond, San Jose, CA (US);
Fareed Nabkel, Concord, CA (US);
Richard Adachi, Castro Valley, CA (US)

(73) Assignee: Lam Research Corporation, Fremont, CA (US)

( * ) Notice: Subject to any disclaimer, the term of this patent is extended or adjusted under 35 U.S.C. 154(b) by 414 days.

(21) Appl. No.: 13/005,989

(22) Filed: Jan. 13, 2011

(65) Prior Publication Data

US 2012/0183200 A1     Jul. 19, 2012

(51) Int. Cl.
*G06K 9/00* (2006.01)

(52) U.S. Cl.
USPC .......................................... 382/145; 382/149

(58) Field of Classification Search
USPC .................................. 382/145, 149
See application file for complete search history.

(56) References Cited

U.S. PATENT DOCUMENTS

| | | | |
|---|---|---|---|
| 5,445,172 A | 8/1995 | Thompson et al. | |
| 5,943,441 A | 8/1999 | Michael et al. | |
| 6,091,498 A * | 7/2000 | Hanson et al. | 356/623 |
| 6,633,331 B1 | 10/2003 | Potter et al. | |
| 6,635,895 B2 | 10/2003 | Haque et al. | |
| 6,825,486 B1 | 11/2004 | Cole et al. | |
| 7,796,807 B2 | 9/2010 | Alumot et al. | |
| 2003/0133604 A1 * | 7/2003 | Neumann | 382/149 |
| 2003/0169916 A1 * | 9/2003 | Hayashi et al. | 382/145 |
| 2004/0018127 A1 | 1/2004 | Long et al. | |
| 2004/0146295 A1 * | 7/2004 | Furman et al. | 398/9 |
| 2004/0218807 A1 * | 11/2004 | Alumot et al. | 382/149 |
| 2005/0129303 A1 * | 6/2005 | Smilansky et al. | 382/149 |
| 2007/0134906 A1 * | 6/2007 | Nygard | 438/618 |

FOREIGN PATENT DOCUMENTS

EP     1628240 B1     3/2008

OTHER PUBLICATIONS

"International Search Report", PCT Application No. PCT/US2012/020185, Mailing Date: May 4, 2012.
"Written Opinion", PCT Application No. PCT/US2012/020185, Mailing Date: May 4, 2012.

* cited by examiner

*Primary Examiner* — Hadi Akhavannik
(74) *Attorney, Agent, or Firm* — IPSG, P.C. Intellectual Property Law (57) ABSTRACT

A method for determining physical placement data for a plurality of wafers is disclosed. The method includes obtaining raw CCD array data from a linear CCD array by clocking data from pixels of the linear CCD array into memory cells of the memory device and ascertaining pixel transition data to determine whether at least one of an upper edge error, a lower edge error, a wafer thickness error, and transition-per-slot error exists. If an error is found, the method includes generating an error signal.

20 Claims, 6 Drawing Sheets

METHODS AND APPARATUS FOR DETECTING MULTIPLE OBJECTS

BACKGROUND OF THE INVENTION

The production of semiconductor products, such as integrated circuits, involves the processing of wafers in a wafer processing system. A plasma processing system is a type of wafer processing machine that employs one or more processing chambers to selectively etch materials from and deposit materials on wafers. To facilitate wafer transport between the atmospheric environment and the more controlled environments within the various processing chambers, load locks are often employed. Wafers are transported by robot arms and positioned on a set of holders, or fingers, in the load lock.

It is possible that in some cases, a wafer among a stack of wafers in the load lock may be incorrectly placed in a slot, or may slip off one of the fingers and falls on a wafer below, or may be missing from a slot, or a wafer may be present in a slot that should not have any wafer in it. In these cases, it is desirable to rapidly acquire wafer physical placement data and to detect abnormalities so that remedial actions may be taken (such as opening to load lock to retrieve the incorrectly positioned wafer) before damage to the wafer and/or to wafer transport sub-assemblies may occur.

Laser micrometers have often been employed for the purpose of determining the aggregate percentage of light in a CCD array that is blocked by a particular object. However, laser micrometers are not well suited for efficiently determining the actual physical locations of multiple discrete objects in their assigned locations as well as the individual physical location data regarding where these objects are located.

In other production or research environments, it is sometimes desirable to rapidly acquire and analyze data regarding the actual physical placement of multiple discrete objects relative to their assigned positions. The present disclosure relates to low-cost, highly efficiency apparatuses and methods for acquiring the actual physical placement data for multiple discrete objects and to efficiently analyze the actual physical placement data with respect to their assigned or expected positions.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

The present invention will now be described in detail with reference to a few embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

Embodiments of the invention relate to low-cost, highly efficient apparatuses and methods for acquiring, storing, and analyzing actual physical placement data for multiple discrete objects with respect to their assigned positions. Although wafer physical placement data in a wafer transport environment is discussed herein, it should be understood that the invention is not limited to wafer placement data, wafer transport, the particular CCD described in the examples, or the wafer processing environment.

In one or more embodiments, a line laser is projected as a sheet of light across a plurality of wafers stacked on fingers. The light is projected at the edge of the stack of spaced-apart wafers, which are disposed in between the laser and a linear array of CCDs (charge coupled devices). The presence of wafers in between the laser and the linear array of CCD blocks the laser light from reaching certain pixels of the CCD array. These pixels are then noted and the set of data, comprising data pertaining to which pixels in the linear array receiving light (e.g., pixels 1-57, 99-138, 190-257, etc.) and which pixels in the linear array failing to receive light (e.g., pixels 58-98, 139-189, etc.), is acquired.

An appropriate threshold, which may be obtained during calibration, may be employed to determine the threshold level of light that delineates whether that pixel should deemed off (i.e., light from the laser is blocked from reaching that pixel) or on (i.e., light from laser is received by that pixel) based on the amount of light that pixel receives.

Further, the linear CCD array is calibrated (e.g., by measurement during installation relative to the physical chamber) such that the position of the CCD array relative to the chamber coordinate system is known. From this array positioning data, the positions of individual CCD array cells in the linear CCD array relative to the chamber coordinate system may be ascertained (e.g., by extrapolating from specification supplied by the manufacturer of the CCD array).

Additionally, the fingers are also calibrated (e.g., by measurement during installation) such that the positions of the sets of fingers relative to the chamber coordinate system are also known. The calibration process also defines the number of slots (which correlates to how many wafers can be accommodated), the locations of the slots, the acceptable light-blockage window within each slot for the upper edge of the wafer and the lower edge of the wafer, etc.

In one or more embodiments, data calibration is accomplished by first adjusting the laser light to the CCD (sensitivity adjustment). In an embodiment, the fingers on which the wafers rest are then calibrated putting a wafer in slot one (either lowest or highest slot) and noting the bottom-of-wafer location from the CCD array data. This may represent, for example, the first on-to-off transition from pixel to pixel in the linear pixel array. The pitch between the parallel sets of fingers is known and thus slot two may be determined by the known pitch between adjacent fingers. Other parameters may then be extrapolated or configured from the data from the wafer in the first slot. These include for example minimum and maximum wafer thickness, top window around the bottom edge of the wafer for each wafer for each slot (e.g., the range of pixel numbers, such as pixel 239 to pixel 264, that the top edge of the wafer in slot two is supposed to occupy), bottom edge window for each wafer in each slot (e.g., the range of pixel numbers, such as pixel 619 to pixel 644, that the bottom edge of the wafer in slot four is supposed to occupy), the filter size (the number of pixels near a off-to-on or on-to-off transition to ignore as possible noise), and the first and last pixel location.

During operation, data is continuously acquired by the CCD array. In one or more embodiments, pixel data (e.g., whether a pixel is off or on) from individual pixels of a CCD array (the entire linear CCD array is referred to herein as a "frame") may be serially clocked out using a master clock. A start signal may indicate the beginning of a frame, and data is serially clocked out pixel-by-pixel for that frame until the entire frame's worth of data has been clocked out. CCD frame data may be continuously or periodically clocked out or clocked out upon request by the processor.

In one or more embodiments, an 8-bit dual port memory is employed to store data from the CCD arrays. To elaborate, dual port memory represents a memory technology that allows data accesses simultaneously by two devices to the memory. Dual port memory is selected for high-speed multiple accesses by both the processor and the CCD arrays, thereby permitting on-the-fly determination by the processor of whether an error condition exists with regard to wafer physical placement.

With an 8-bit dual port memory, up to 8 separate CCD arrays (implementing 8 sensors) may be accommodated simultaneously. However, larger memories may be employed if more CCD arrays need to be accommodated. Data from the arrays can be clocked simultaneously using a master clock and a common start signal (or other synchronizing mechanism). Logic (such as a complex programmable logic device) may then be employed to acquire the serial data from the CCD arrays and pack the data into words (8-bit, 16-bit etc.) in registers for storing the data in the dual-port memory. For example, bit 0 may be employed to carry data from pixel n from array 0, bit 1 may be employed to carry data from the same pixel n from array 1, bit 2 may be employed to carry data from the same pixel n from array 2, and so forth.

The raw CCD array data may then be used to determine the percentage of pixels that are off or on, the number of pixels that are off or on, as well as the specific pixels in the linear CCD array that are off or on and transitions (off to on and on to off). This data, filtered or unfiltered, may be employed to ascertain wafer presence in a slot, apparent wafer thickness, apparent wafer placement within a slot, whether a wafer occupies more than one slot, whether there are error conditions pertaining to one or more wafers in the wafer transport environment, etc.

Since the locations of the pixels are mapped to the chamber coordinate system beforehand, and acceptable windows for top and bottom wafer edges as well as error conditions are predefined for each slot, these mappings, window definitions, and error conditions may be applied against the set of pixel data of a frame to efficiently determine the physical placement data of wafers in slots in the wafer transport environment as well as to determine whether an error condition exists that warrant remedial actions such as stopping the wafer transport and extracting incorrectly positioned wafers.

Figure 1:
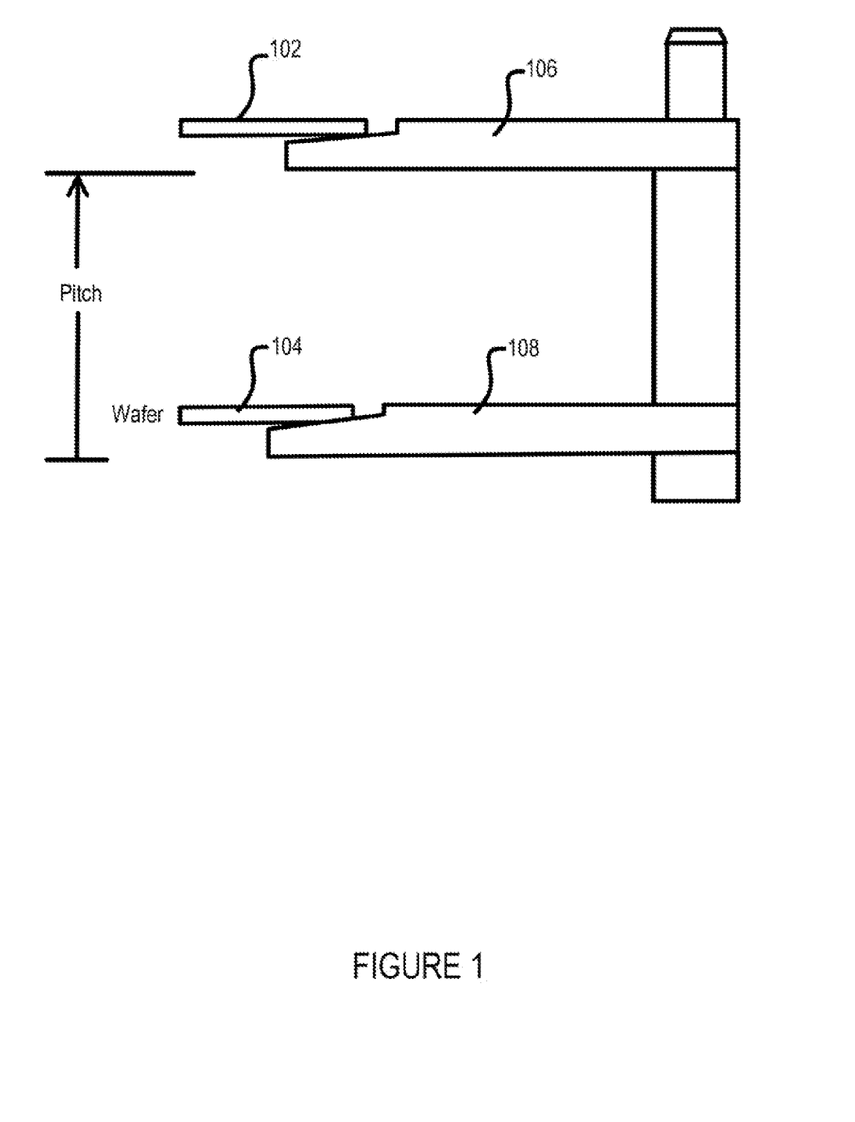
FIG. 1 shows one example placement on wafers on fingers in a load lock.

The features and advantages of the invention may be better understood with reference to the figures and discussions that follow. FIG. 1 shows one example whereby wafers 102 and 104 are positioned on fingers 106 and 108 in the load lock. These sets of fingers (typically 3 per wafer) form "slots" and the wafers are placed in these parallel and spaced-apart slots awaiting transport among the various chambers for processing.

Figure 2:
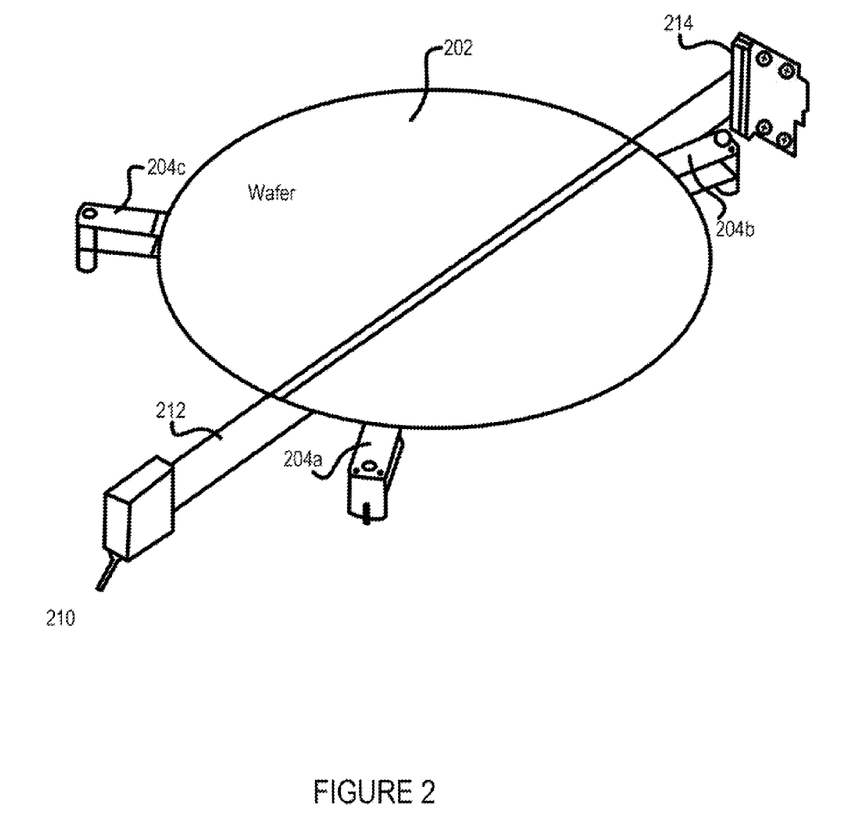
FIG. 2 shows, in accordance with an embodiment of the invention, an example system for acquiring, storing, and analyzing actual physical placement data for multiple wafers with respect to their slots in a transport environment.

FIG. 2 shows, in accordance with an embodiment of the invention, an example system for acquiring, storing, and analyzing actual physical placement data for multiple wafers with respect to their slots in a transport environment.

With reference to FIG. 2, a wafer 202 is shown disposed on a set of fingers comprising 204*a*, 204*b*, and 204*c* in an example load lock chamber. While two parallel sets of fingers are shown, the number of sets of fingers may vary. A line laser 210 projects a beam of light 212 toward a linear CCD array 214. In the example of FIG. 2, CCD array 214 is a 1×768 array although different arrays may be employed if more or less data granularity is desired. During operation, wafers disposed on the parallel sets of fingers block a portion of the light projected by laser 210. As a result, some of the pixels in CCD array 214 would be on (unblocked) while others would be off (blocked).

Figure 3A:
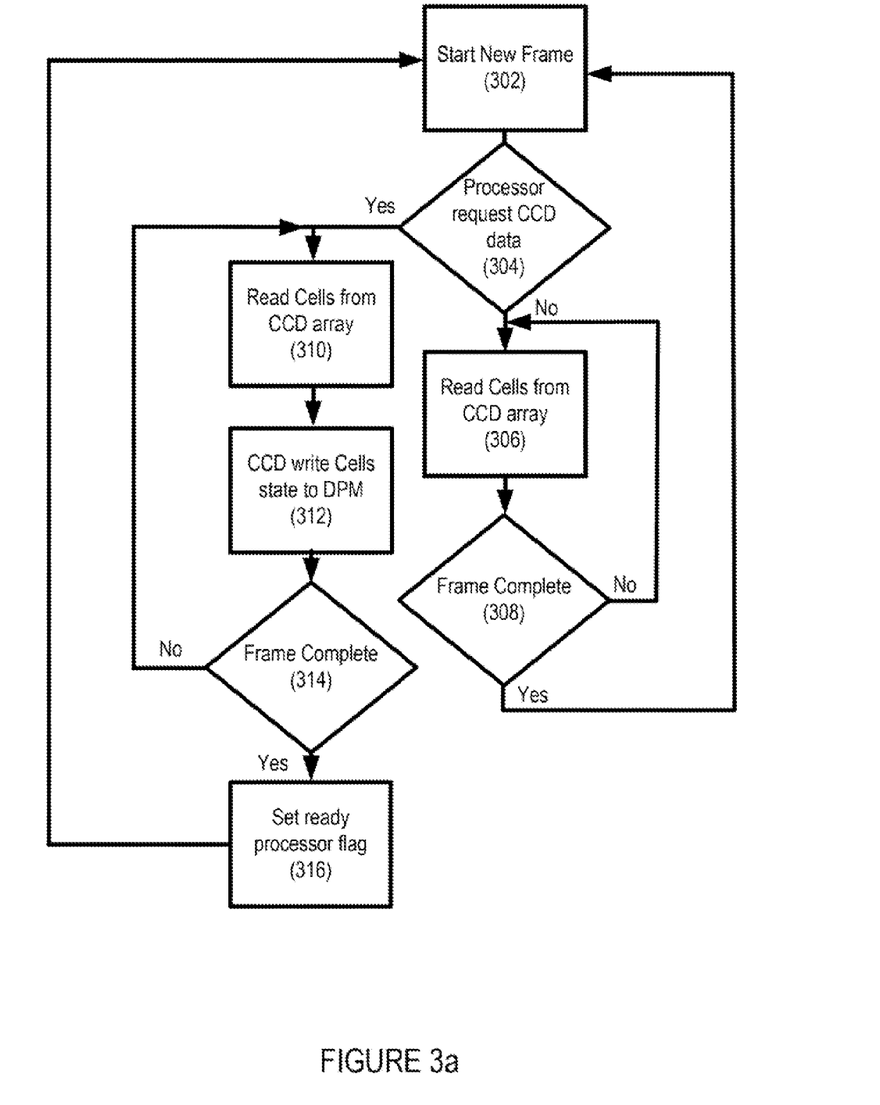
FIG. 3A shows an example flow diagram for collecting data from the CCD arrays.

FIG. 3*a* shows an example flow diagram for collecting data from the CCD arrays. The data is collected frame by frame (decisions 304, and 314). Generally speaking, data is updated continuously in the cells of the CCD array as laser light shines on the pixels of the CCD array (step 306). If the data is requested by the processor (304), the data is read from the cells in the CCD array (310) and written to the dual port memory (312). Once the entire frame is written (314) to the dual port memory, a ready flag may be set with the processor (step 316).

Figure 3B:
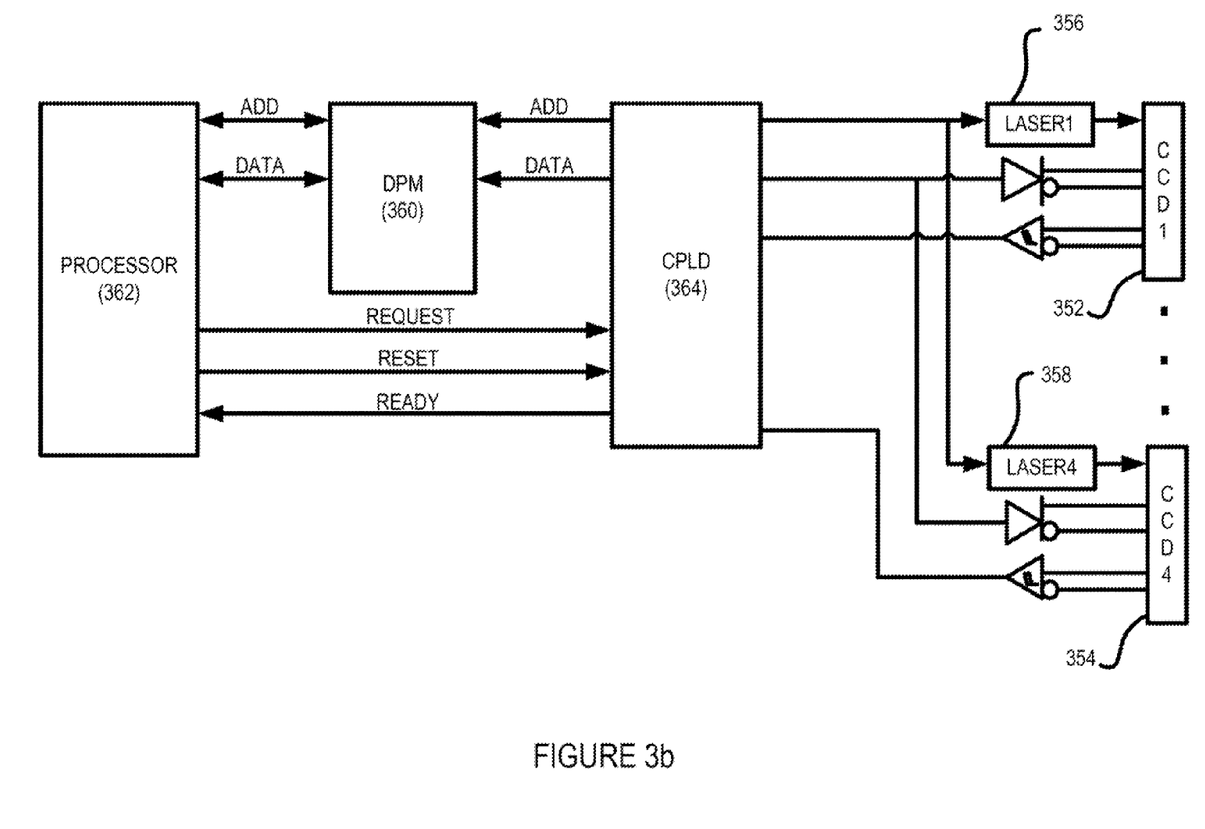
FIG. 3B shows a simplified circuit diagram of the data acquisition, storage, and analysis arrangement.

FIG. 3B shows a simplified circuit diagram of the data acquisition, storage, and analysis arrangement involving 2 CCD arrays 352 and 354, lasers 356 and 358, dual port memory 360, processor 362, and a programmable logic device 364 (implemented by a complex programmable logic device in the example of FIG. 3B although any suitable programmable logic device or custom IC or hardware/software combination may be employed). Dual port memory 360 is shown accessed by both complex programmable logic device 364 (for updating pixel data into the memory) and by processor 362 (to obtain pixel/frame data for analysis). Depending on implementation, one or both of complex programmable logic device 364 and processor 362 may perform filtering and/or data analysis as desired.

Figure 4:
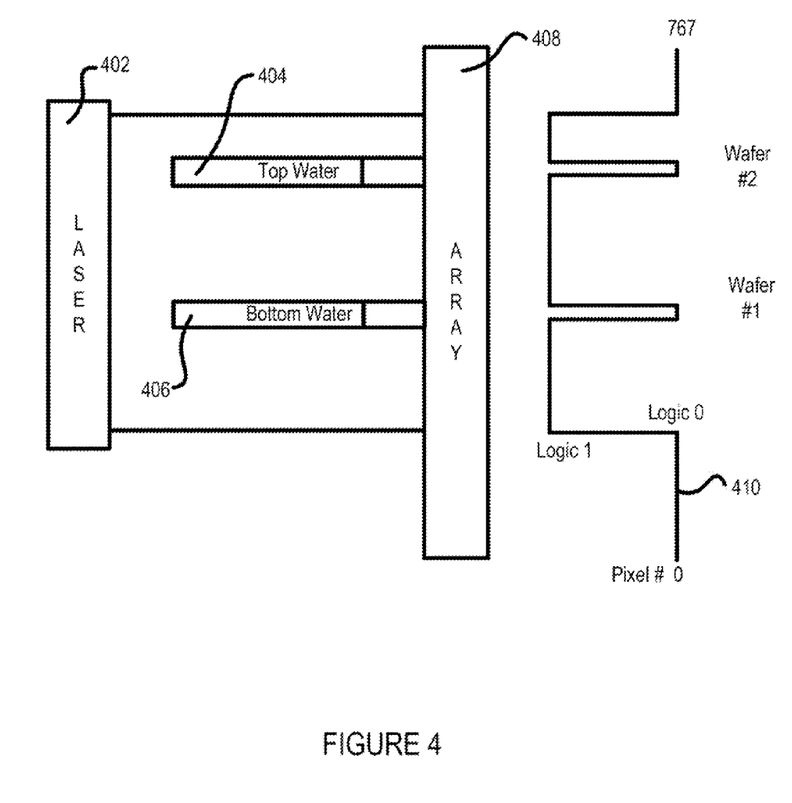
FIG. 4 shows a simplified conceptual drawing of the laser, the wafers, the CCD array, and the resulting data frame.

FIG. 4 shows a simplified conceptual drawing of the laser 402, the wafers 404 and 406, the CCD array 408, and the resulting data frame 410. Pixels that are blocked by the wafers are off (logic 0 in the example of FIG. 4) while pixels that are not blocked by the wafers are on (logic 1 in the example of FIG. 4). Although a 1×768 pixel array is employed in the example of FIG. 4, any suitable array size may be employed.

With reference to FIG. 2, generally speaking, the position of CCD array 214 relative to the chamber coordinate system is fixed and known. Since the specification of CCD array 214, including the dimensional data and positional data of individual pixels therein, is known, the actual position of individual pixels relative to the chamber coordinate system is also known. Further, the positions of the sets of fingers 204*a*, 204*b* and 204*c* are set and known relative to the chamber coordinate system. The finger positional data define slots within which wafers may be disposed. From these data sets, it is possible to derive actual physical placement data for the wafers from the pixel on/off data for individual pixels of CCD array 214, relative to the chamber coordinate system.

Figure 5:
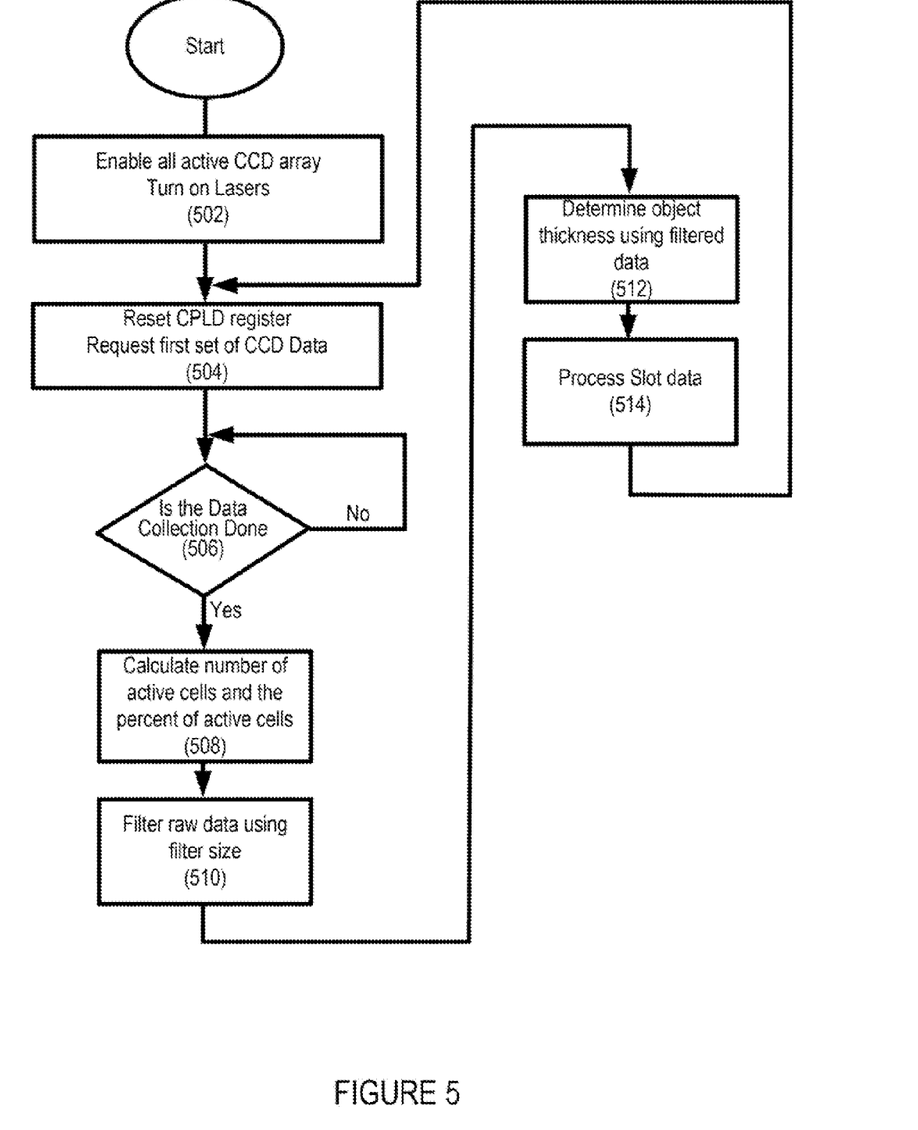
FIG. 5 shows, in accordance with an embodiment of the invention, a flowchart for acquiring and analyzing actual physical placement data for multiple wafers with respect to their multiple slots in a transport environment.

FIG. 5 shows, in accordance with an embodiment of the invention, a flowchart for acquiring and analyzing actual physical placement data for multiple wafers with respect to their multiple slots in a transport environment. In step 502, the active CCD arrays are enabled and lasers are turned on. As discussed, up to 8 CCD arrays and 8 lasers may be accommodated by an 8-bit dual port memory structure, for example.

In step 504, the register of the complex programmable logic device is reset and the first set of CCD data is requested (see FIG. 3b). If data collection is done for the entire frame (506), the process next calculates the number of active cells and the percentage of active cells (508). Filtering may also be performed (510) on the raw data set, as discussed earlier. In step 512, the object thickness may be determined. In step 514, other slot-related calculations may be performed. Some example data calculations in steps 512 and 514 are further elaborated below.

To elaborate, other data, including error alerts, may be acquired, in one or more embodiments, by detecting transitions and determining wafer presence in slots. A pixel transition represents an on-to-off or off-to-on transition in the frame data. In one or more embodiments, a filter may be implemented on the raw frame data to minimize noise. To minimize false transitions, the processor may be configured, for example, to filter the unwanted transitions according to a filter size. For example, a filter size value (e.g., 0-255) may tell the processor how many pixels to ignore after capturing a transition. As an example, if the bottom of wafer #1 is detected at pixel #300 and the filter size is set to the default of 4, transitions that occur within the next 4 pixels are ignored. If there is a transition on the fifth pixel from pixel #300, that transition on the fifth pixel from pixel #300 will be captured. In this manner, a highly efficient filtering mechanism is implemented. Other filtering schemes may also be implemented. Data analysis described herein may operate on the raw or filtered data set as desired.

A state machine may be implemented on the frame data to track pixel transitions. If there are fewer or greater numbers of transitions than expected in the array or in one or more slots, an error flag denoting that condition may be set. For example, if there are more than two transitions (e.g., on-to-off and off-to-on) in a single slot, an error condition may exist since the data indicates that multiple wafers may be in a single slot (e.g., when an upper wafer slides off one of the fingers and rests on a lower wafer). As another example, if there are no transitions in a slot where there is supposed to be a wafer, an error flag may be set. If the sequence or number of transitions is illogical either in the data frame or in one of the slots, an error flag denoting that condition may be set as well.

Further, adjacent pairs of on-to-off (representing a transition from unblocked to blocked pixels) and off-to-on (representing a transition from blocked to unblocked pixels) may be examined to determine wafer thickness. If the wafer is unexpectedly thick, for example, this may signal the presence of more than one wafer. In this case, an error flag signifying that condition may be set. The wafer thickness data may also be employed to ascertain wafer temperature, for example, since apparent wafer thickness (bowing) may vary due to temperature.

In one or more embodiments, bounds or limits on the allowable position for the lower edge of the wafer associated with a slot may be set. After calibration a bottom edge window may be defined. The bottom edge window may have a bottom edge minimum and bottom edge maximum, where bottom edge minimum represents the lowest allowable position for the wafer lower surface for that slot and the bottom edge maximum represents the highest allowable position for the wafer lower surface for that slot. If the wafer lower edge (detected by the state machine from a valid transition that signifies the wafer lower surface in that slot) is outside of the bottom edge window, an error flag signifying that condition may be set.

In one or more embodiments, bounds or limits on the allowable position for the upper edge of the wafer associated with a slot may be set. After calibration a top edge window may be defined. The top edge window may have a top edge minimum and top edge maximum, where top edge minimum represents the lowest allowable position for the wafer upper surface for that slot and the top edge maximum represents the highest allowable position for the wafer upper surface for that slot. If the wafer upper edge (detected by the state machine from a valid transition that signifies the wafer upper surface in that slot) is outside of the top edge window, an error flag signifying that condition may be set.

The wafer position data may be employed to ascertain wafer bow, for example, if the beam of light is appropriately positioned. Wafer sag may be due to temperature or other chamber conditions, and the wafer bow data may be employed to ascertain temperature or the existence of certain chamber conditions.

In one or more embodiments, if a transition representing the wafer upper surface is in one slot and the next transition representing the wafer lower surface is in another slot, an error flag signifying that condition may be set. Conversely, if a transition representing the wafer lower surface is in one slot and the next transition representing the wafer upper surface is in another slot, an error flag signifying that condition may be set.

Having disclosed exemplary embodiments and the best mode, modifications and variations may be made to the disclosed embodiments while remaining within the subject and spirit of the invention as defined by the following claims.

The invention claimed is:

1. A method for determining physical placement data for a plurality of wafers, said plurality of wafers being disposed on a plurality of parallel sets of fingers using a linear CCD array and a memory device and a logic module, comprising:
   obtaining raw CCD array data, said obtaining including serially clocking data from pixels of said linear CCD array into memory cells of said memory device;
   ascertaining, using said logic module and said memory device, pixel transition data from at least one of said raw CCD array data and filtered CCD array data, said pixel transition data including a number of transitions between adjacent pixel pairs and locations of said transitions;
   ascertaining, using said logic module and said pixel transition data, whether at least one of an upper edge error, a lower edge error, a wafer thickness error, and transition-per-slot error exists; and
   if said at least one of said upper edge error, said lower edge error, said wafer thickness error, and said transition-per-slot error exists, generating an error signal.

2. The method of claim 1 further comprising filtering said raw CCD data to obtain said filtered CCD array data, wherein said ascertaining said pixel transition data employs said filtered CCD array data.

3. The method of claim 1 further comprising ascertaining, using said logic module, wafer edge data from said pixel transition data, said wafer edge data including pixel positions representing at least upper edges of individual ones of said plurality of wafers, wherein said upper edge error is deemed to exist if any of said upper edges violate predefined upper allowable windows for said upper edges, said predefined upper allowable windows defining pixel zones within which a presence of one of said upper edges is permissible.

4. The method of claim 1 further comprising ascertaining, using said logic module, wafer edge data from said pixel transition data, said wafer edge data including pixel positions representing at least lower edges of individual ones of said plurality of wafers, wherein said lower edge error is deemed to exist if any of said lower edges violate predefined upper allowable windows for said lower edges, said predefined lower allowable windows defining pixel zones within which a presence of one of said lower edges is permissible.

5. The method of claim 1 further comprising ascertaining, using said logic module, wafer edge data from said pixel transition data, said wafer edge data including pixel positions representing at least upper edges and lower edges of individual ones of said plurality of wafers, wherein said wafer thickness error is deemed to exist if a difference between an upper edge and a lower edge of at least one of said plurality of wafers exceeds a predefined threshold.

6. The method of claim 1 wherein said logic module is a processor.

7. The method of claim 1 wherein said memory device is a dual-port memory device.

8. The method of claim 1 wherein a transition of said transitions is determined using a predefined threshold to ascertain whether is pixel is blocked or unblocked.

9. The method of claim 1 wherein said transition-per-slot error includes a more-than-expected number of transitions for a given slot.

10. The method of claim 1 wherein said transition-per-slot error includes a fewer-than-expected number of transitions for a given slot.

11. In a plasma processing system, a method for determining physical placement data for a plurality of wafers, comprising:
   placing a plurality of wafers on a plurality of parallel sets of fingers;
   illuminating a linear CCD array using a light source, the plurality of wafers being disposed between the linear CCD array and the light source;
   obtaining raw CCD array data, said obtaining including serially clocking data from pixels of said linear CCD array into memory cells of a memory device;
   ascertaining, using a logic module and said memory device, pixel transition data from at least one of said raw CCD array data and filtered CCD array data, said pixel transition data including at least a number of transitions between adjacent pixel pairs and locations of said transitions; and
   ascertaining, using said logic module and said pixel transition data, whether at least one of an upper edge error, a lower edge error, a wafer thickness error, and transition-per-slot error exists;
   if said at least one of said upper edge error, said lower edge error, said wafer thickness error, and said transition-per-slot error exists, generating an error signal.

12. The method of claim 11 further comprising filtering said raw CCD data to obtain said filtered CCD array data, wherein said ascertaining said pixel transition data employs said filtered CCD array data.

13. The method of claim 11 further comprising ascertaining, using said logic module, wafer edge data from said pixel transition data, said wafer edge data including pixel positions representing at least upper edges of individual ones of said plurality of wafers, wherein said upper edge error is deemed to exist if any of said upper edges violate predefined upper allowable windows for said upper edges, said predefined upper allowable windows defining pixel zones within which a presence of one of said upper edges is permissible.

14. The method of claim 11 further comprising ascertaining, using said logic module, wafer edge data from said pixel transition data, said wafer edge data including pixel positions representing at least lower edges of individual ones of said plurality of wafers, wherein said lower edge error is deemed to exist if any of said lower edges violate predefined upper allowable windows for said lower edges, said predefined lower allowable windows defining pixel zones within which a presence of one of said lower edges is permissible.

15. The method of claim 11 further comprising ascertaining, using said logic module, wafer edge data from said pixel transition data, said wafer edge data including pixel positions representing at least upper edges and lower edges of individual ones of said plurality of wafers, wherein said wafer thickness error is deemed to exist if a difference between an upper edge and a lower edge of at least one of said plurality of wafers exceeds a predefined threshold.

16. The method of claim 11 wherein said logic module is a processor.

17. The method of claim 11 wherein said memory device is a dual-port memory device.

18. The method of claim 11 wherein a transition of said transitions is determined using a predefined threshold to ascertain whether is pixel is blocked or unblocked.

19. The method of claim 11 wherein said transition-per-slot error includes a more-than-expected number of transitions for a given slot.

20. The method of claim 11 wherein said transition-per-slot error includes a fewer-than-expected number of transitions for a given slot.

* * * * *